(12) United States Patent
Janssen et al.

(10) Patent No.: US 10,364,002 B2
(45) Date of Patent: Jul. 30, 2019

(54) WATER LOCK TO PREVENT WATER INGRESS

(71) Applicant: KONINKLIJKE PHILIPS N.V., Eindhoven (NL)

(72) Inventors: Esther Anna Wilhelmina Gerarda Janssen, Waalre (NL); Bart Andre Salters, Eindhoven (NL); Roelant Boudewijn Hietbrink, Utrecht (NL); Cornelis Gerardus Visser, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/747,456

(22) PCT Filed: Jul. 20, 2016

(86) PCT No.: PCT/EP2016/067223
§ 371 (c)(1),
(2) Date: Jan. 25, 2018

(87) PCT Pub. No.: WO2017/016940
PCT Pub. Date: Feb. 2, 2017

(65) Prior Publication Data
US 2018/0215450 A1 Aug. 2, 2018

(30) Foreign Application Priority Data
Jul. 30, 2015 (EP) ...................................... 15179082

(51) Int. Cl.
*B63B 59/04* (2006.01)
*B63B 59/08* (2006.01)
(Continued)

(52) U.S. Cl.
CPC ................ *B63B 59/04* (2013.01); *A61L 2/10* (2013.01); *B01J 19/123* (2013.01); *B08B 17/02* (2013.01);
(Continued)

(58) Field of Classification Search
CPC .. B63B 59/04; B63B 59/08; A61L 2/10; B01J 19/123; B08B 17/02; C02F 1/325; C02F 2303/20
(Continued)

(56) References Cited

U.S. PATENT DOCUMENTS

2003/0001112 A1* 1/2003 Hollander ................. A61L 2/10
250/504 R
2009/0270526 A1 10/2009 Liu et al.
(Continued)

FOREIGN PATENT DOCUMENTS

AU 2010200827 A1 9/2011
GB 2470350 A 11/2010
(Continued)

*Primary Examiner* — Nicole M Ippolito

(57) ABSTRACT

The invention provides an element (210) comprising: (i) an electrical component (1220); (ii) an optical medium (270) comprising medium material (275) comprising a silicone transmissive for one or more of UV radiation and visible radiation, wherein the electrical component (1220) is embedded in the optical medium (270); (iii) an electrical connector (510) for functionally coupling the electrical component (1220) external to the optical medium (270), wherein the electrical connector (510) is embedded in the optical medium (270) over at least part of its length; and (iv) a water barrier (530) at least partly embedded in the optical medium (270) and configured to enclose at least part of the electrical connector (510).

15 Claims, 6 Drawing Sheets

(51) Int. Cl.
  *B01J 19/12* (2006.01)
  *B08B 17/02* (2006.01)
  *A61L 2/10* (2006.01)
  *C02F 1/32* (2006.01)

(52) U.S. Cl.
  CPC .............. *B63B 59/08* (2013.01); *C02F 1/325* (2013.01); *C02F 2303/20* (2013.01)

(58) Field of Classification Search
  USPC .......................................... 250/493.1, 504 R
  See application file for complete search history.

(56) References Cited

U.S. PATENT DOCUMENTS

2012/0002417 A1  1/2012  Li
2013/0048877 A1  2/2013  Thoren et al.

FOREIGN PATENT DOCUMENTS

| JP | 5023502 A | 2/1993 |
| WO | 2007122534 A1 | 11/2007 |
| WO | 2010052449 A1 | 5/2010 |
| WO | 2013157436 A1 | 10/2013 |
| WO | 2013182077 A1 | 12/2013 |
| WO | 2014188347 A1 | 11/2014 |
| WO | 2016001227 A1 | 1/2016 |

\* cited by examiner

WATER LOCK TO PREVENT WATER INGRESS

CROSS-REFERENCE TO PRIOR APPLICATIONS

This application is the U.S. National Phase application under 35 U.S.C. § 371 of International Application No. PCT/EP2016/067223, filed on 20 Jul. 2016, which claims the benefit of European Patent Application No. 15179082.1, filed on 30 Jul. 2015. These applications are hereby incorporated by reference herein.

FIELD OF THE INVENTION

The invention relates to an element including an electrical component, such as a light source for providing element radiation in the UV and/or visible, especially UV. The invention further relates to a system, such as an anti-biofouling system, comprising such element. The invention also relates to an object comprising such element. Yet further, the invention also relates to a method for applying such element to such object and to a method for providing such element per se.

BACKGROUND OF THE INVENTION

Anti-biofouling methods are known in the art. US2013/0048877, for instance, describes a system for anti-biofouling a protected surface, comprising an ultraviolet light source configured to generate ultraviolet light, and an optical medium disposed proximate to the protected surface and coupled to receive the ultraviolet light, wherein the optical medium has a thickness direction perpendicular to the protected surface, wherein two orthogonal directions of the optical medium orthogonal to the thickness direction are parallel to the protected surface, wherein the optical medium is configured to provide a propagation path of the ultraviolet light such that the ultraviolet light travels within the optical medium in at least one of the two orthogonal directions orthogonal to the thickness direction, and such that, at points along a surface of the optical medium, respective portions of the ultraviolet light escape the optical medium.

US2009/270526 describes an encapsulant composition, including at least one resin monomer, a filler and a photo initiator, wherein the at least one resin monomer is selected from the group consisting of acrylic resin monomer, epoxy resin monomer, silicone resin monomer and compositions thereof, and the filler is of about 0.1~15 weight % of the encapsulant composition.

WO2014/188347 describes a method of anti-fouling of a surface while said surface is at least partially submersed in an liquid environment, the method comprising providing an anti-fouling light, distributing at least part of the light through an optical medium comprising a silicone material and/or UV grade fused silica, and emitting the anti-fouling light from the optical medium and from the surface.

WO2016/001227 describes an anti-fouling lighting system for preventing or reducing biofouling on a fouling surface of an object, by providing an anti-fouling light via an optical medium to said fouling surface, the anti-fouling lighting system comprising (a) a lighting module comprising (i) a light source configured to generate an anti-fouling light, and (ii) said optical medium configured to receive at least part of the anti-fouling light, the optical medium comprising an emission surface configured to provide at least part of said anti-fouling light, and (b) a control system configured to control an intensity of the anti-fouling light as function of one or more of (i) a feedback signal related to a biofouling risk and (ii) a timer for time-based varying the intensity of the anti-fouling light.

WO2013/157436 describes an adhesive tape for preventing aquatic biofouling, which can prevent discoloration or degradation of an adherent, to which said adhesive tape for preventing aquatic biofouling is adhered, caused by exposure to ultraviolet rays and so on. The adhesive tape for preventing aquatic biofouling comprises an antifouling layer, a substrate layer and an adhesive layer in this order, wherein at least one layer selected from the aforesaid antifouling layer, substrate layer and adhesive layer contains a weathering agent.

SUMMARY OF THE INVENTION

Biofouling or biological fouling (herein also indicated as "fouling") is the accumulation of microorganisms, plants, algae, and/or animals on surfaces. The variety among biofouling organisms is highly diverse and extends far beyond attachment of barnacles and seaweeds. According to some estimates, over 1700 species comprising over 4000 organisms are responsible for biofouling. Biofouling is divided into microfouling which includes bio film formation and bacterial adhesion, and macrofouling which is the attachment of larger organisms. Due to the distinct chemistry and biology that determine what prevents organisms from settling, these organisms are also classified as hard or soft fouling types. Calcareous (hard) fouling organisms include barnacles, encrusting bryozoans, mollusks, polychaete and other tube worms, and zebra mussels. Examples of non-calcareous (soft) fouling organisms are seaweed, hydroids, algae and biofilm "slime". Together, these organisms form a fouling community.

In several circumstances biofouling creates substantial problems. Machinery stops working, water inlets get clogged, and hulls of ships suffer from increased drag. Hence the topic of anti-fouling, i.e. the process of removing or preventing fouling from forming, is well known. In industrial processes, bio-dispersants can be used to control biofouling. In less controlled environments, organisms are killed or repelled with coatings using biocides, thermal treatments or pulses of energy. Non-toxic mechanical strategies that prevent organisms from attaching include choosing a material or coating with a slippery surface, or creation of nanoscale surface topologies similar to the skin of sharks and dolphins which only offer poor anchor points. Biofouling on the hull of ships causes a severe increase in drag, and thus increased fuel consumption. It is estimated that an increase of up to 40% in fuel consumption can be attributed to biofouling. As large oil tankers or container transport ships can consume up to €200.000 a day in fuel, substantial savings are possible with an effective method of anti-biofouling.

It surprisingly appears that one may effectively use UV radiation to substantially prevent biofouling on surfaces that are in contact with sea water or water in lakes, rivers, canals, etc. . . . Herewith, an approach is presented based on optical methods, in particular using ultra-violet light or radiation (UV). It appears that most micro-organisms are killed, rendered inactive or unable to reproduce with sufficient UV light. This effect is mainly governed by the total dose of UV light. A typical dose to kill 90% of a certain micro-organism is 10 mWh/m$^2$.

To prevent biofouling systems and elements may be applied that come at least temporarily into contact with (sea)

water. It appears that silicones can be used as conformal coating to protect electronics from moisture in applications that can come in contact with moisture, either in the liquid form or as vapor. Other protecting materials are epoxies, acrylates, polyurethanes or parylene. Optical electronic applications like outdoor lighting with light emitting diodes (LEDs) need to be protected from the wet environment. This can be done by sealing a rigid glass window in the luminaire housing. The powering cable may also be sealed with waterproof gaskets. Waterproof LED strips for outdoor use can be protected by a transparent coating, which can be silicone, acrylate or polyurethane.

For these applications protection is needed to prevent moisture accumulating around the circuitry, LEDs and other components, causing corrosion and eventually failure.

Herein, amongst others a web of LEDs soldered to electrical wires completely embedded in silicone is proposed, to make a thin, flexible, large area sheet of light. When UV-LEDs are used in this product concept, it can be used under water as anti-fouling system. If the LEDs and electronics are embedded well in silicone, they are protected from the liquid (sea) water. Water vapor will migrate into the silicone, but as long as the silicone surrounds the LEDs and wires, it is believed that corrosion will not occur. If the silicone delaminates from the wires and the components, moisture can condensate at the interface and cause corrosion. It however appeared that the weakest link is the powering cable that has to leave the silicone sheet. Moisture can creep along the interface of the cable and the silicone, or along the inside of the cable. This leads to surprisingly serious problems.

For the anti-fouling application, highly optically (UV) transparent silicones are a desired embodiment. Such silicones appear to have little adhesion to many materials.

Hence, it is an aspect of the invention to provide an alternative element or system for providing anti-fouling radiation, which preferably further at least partly obviate one or more of above-described drawbacks. More in general, it is an aspect to provide an electrical component protected for water.

An option could be to use adhesion promoters. This would improve adhesion of the silicone to the electrical cables. However, it appears that adding adhesion promoters is not preferred because they absorb light in the UV-range, thereby decreasing transmission and efficiency. Another option could be to change to another medium material, other than silicones. However, it appears that silicones, especially dimethyl silicones have optical properties and physical properties that are superior for the presently desired applications. Hence, this invention proposes a water lock on the cable and/or electronics, which prevents moisture ingress towards the embedded electronics that are sensitive for corrosion. The water lock is made of a material (or materials) that adhere(s) very well on one hand to the cable or components and on the other hand to the optical silicone.

Therefore, in a first aspect the invention provides an element comprising (i) an electrical component, (ii) an optical medium comprising medium material, especially a medium material transmissive for one or more of UV radiation (100-400 nm) and visible radiation (400-780 nm), such as a silicone (i.e. an optical transmissive silicone), wherein the electrical component is embedded in the (optical) medium ("medium"), (iii) an electrical connector ("connector") for functionally coupling the electrical component external to the optical medium, wherein the electrical connector is embedded in the optical medium over at least part of its length, and (iv) a water barrier at least partly embedded in the optical medium and configured to enclose at least part of the electrical connector.

Referring to applications wherein visible and/or UV radiation is applied, the invention further especially provides such element, configured to provide element radiation comprising one or more of UV radiation and visible radiation, the element comprising (i) said electrical component comprising a light source configured to provide light source radiation in one or more of the UV and the visible wavelength ranges, (ii) said optical medium, wherein the light source is embedded in the optical medium, (iii) said electrical connector for functionally coupling the light source with a source of electrical power external from the optical medium, wherein the electrical connector comprises a first connector part ("first connector part") embedded in the optical medium and an interface connector part where the first connector part is physically accessible from external from the optical medium, and (iv) said water barrier. Therefore, in yet a further embodiment the invention also provides an element configured to provide element radiation (i.e. radiation escaping from the element) comprising one or more of UV radiation and visible radiation, the element comprising (i) a light source configured to provide light source radiation in one or more of the UV and the visible wavelength ranges (which is used as element radiation and/or converted into element radiation), (ii) an optical medium comprising medium material, the medium material in embodiments especially comprising a silicone, transmissive for the light source radiation (and (thus) especially also transmissive for element radiation), wherein the light source is embedded in the optical medium, (iii) an electrical connector for functionally coupling the light source with a source of electrical power external from the optical medium, wherein the electrical connector comprises a first connector part embedded in the optical medium and an interface connector part physically accessible from external from the optical medium; and (iv) a water barrier ("barrier" or "water stop") at least partly embedded in the optical medium and configured to enclose at least part of the first connector part of the electrical connector and in embodiments configured adjacent to the interface connector part.

With such element, the electrical component may be protected from contact with water. Water ingress (from outside the medium) creeping along the electrical connector to the electrical component is reduced or even completely inhibited.

The term "electrical component" may especially refer to an electronic component. The electronic component may include an active or a passive electronic component. An active electronic component may be any type of circuit component with the ability to electrically control electron flow (electricity controlling electricity). Examples thereof are diodes, especially light emitting diodes (LED). LEDs are herein also indicated with the more general term solid state lighting devices or solid state light sources. Hence, in embodiments the electronic component comprises an active electronic component.

Especially, the electronic component comprises a solid state light source. Other examples of active electronic components may include power sources, such as a battery, a piezo-electric device, an integrated circuit (IC), and a transistor. In yet other embodiments, the electronic component may include a passive electronic component. Components incapable of controlling current by means of another electrical signal are called passive devices. Resistors, capacitors, inductors, transformers, etc. can be considered passive devices.

In an embodiment, the electronic component may include an RFID (Radio-frequency identification) chip. A RFID chip may be passive or active. Especially, the electronic component may include one or more of a solid state light source (such as a LED), a RFID chip, and an IC.

The term "electronic component" may also refer to a plurality of alike or a plurality of different electronic components.

In specific embodiments, the electrical component may e.g. comprise one or more of a battery, a sensor, a light source, a processor, etc. etc. . . . The electrical component especially comprises a functional component. The electrical connector, such as a (conventional) electrical cable, is especially not considered an electrical component herein. The term "electrical component" may also refer to a plurality of electrical components. The invention is further especially explained with reference to a light source as example of electrical component.

With such element, for instance element radiation may be provided under humid conditions or with the element at least partly submerged into water, with a high light extraction, especially due to the relative highly transmissive medium material, and with a long lifetime, especially due to the water barrier. The water barrier is especially configured as intermediate material that forms a barrier against water creeping along wires because of the good adhesion of the water barrier to the cable (or other electrical connector) or components on one hand and the embedding silicone, or other material, on the other hand. The electrical connector will in general comprise an insulator surrounding an electrically conductive material (such as copper), such as in the case of an electrical cable, with the insulator especially being a polymeric material, such as an epoxide, etc. . . . Such insulating material and the silicone do in general not adhere well. A suitable elastic weather resistant cable mantel material is e.g. polyurethane. An electrical cable may especially comprises two or more wires running side by side and bonded, twisted, or braided together to form a single assembly. However, an electrical cable may also comprise a single wire with a single electrically conductive core. In such instance, the electrical component may have to be connected to two (or more) different electrical cables.

The element is especially configured to provide one or more of UV and visible radiation. The UV radiation may especially be of relevance for anti-fouling applications. The visible radiation may especially be of relevance for lighting applications, including e.g. advertisement applications.

The terms "visible", "visible light" or "visible emission" often refer to light having a wavelength in the range of about 380-780 nm. Here, however, UV radiation is defined as the range of 100-400 nm, and visible is herein used for the wavelength range of 400-780 nm. Visible light may be created by light sources providing visible light and/or light sources providing UV radiation which is at least partly converted into visible radiation by a converter material, such as a luminescent material. Herein, the invention is further especially explained in relation to UV application, such as for anti-fouling purposes in amongst others marine applications. Hence, in an embodiment the element is configured to provide element radiation comprising UV radiation.

The element may be comprised in an anti-biofouling system, or more in general a system that may be configured to provide radiation (under conditions that may be humid or at least temporarily submerged in water). Hence, in a further aspect, the invention also provides a (anti-biofouling) system comprising the element as defined herein and optionally a control system configured to control element radiation from said element. Further, the anti-biofouling system may optionally include an electrical power source. However, the electrical power source is not necessarily comprised by the element or anti-bio fouling system, respectively.

The element and/or the (anti-biofouling) system may especially be applied on or in objects that are during use in contact with water, such as seawater, or which are applied in humid conditions, such as e.g. at a shore or other outdoor applications. Hence, in yet a further aspect the invention also provides an object, that especially during use is at least partly submerged in water, the object further comprising an element as defined herein, or especially an (anti-biofouling) system comprising said element as defined herein, said element (or said system) associated to an external surface of said object, wherein the object may especially be selected from the group consisting of a vessel and an infrastructural object, wherein the object further comprises an electrical power source configured to provide electrical power to the light source. Other embodiments (of objects) however, may e.g. include (under water) lamps, outdoor lamps, such as for use in (at least temporarily) relative humid areas, such as in tropical rain forests, mousson areas, etc. . . .

Herein, the phrase "object that during use is at least partly submerged in water" especially refers to objects such as vessels and infrastructural objects that have aquatic applications. Hence, during use such object will be in general in contact with the water, like a vessel in the sea, a lake, a canal, a river, or another waterway, etc. . . . The term "vessel" may e.g. refer to e.g. a boat or a ship, etc., such as a sail boat, a tanker, a cruise ship, a yacht, a ferry, a submarine, etc. etc. . . . The term "infrastructural object" may especially refer to aquatic applications that are in general arranged substantially stationary, such as a dam, a sluice, a pontoon, an oilrig, etc. etc. . . .

The term "external surface" especially refers to the surface that may be in physical contact with water. Hence, instead of the term "external surface" also the term "fouling surface" may be applied. Further, in such embodiments the term "water line" may also refer to e.g. filling level. Especially, the object is an object configured for marine applications, i.e. application in or near to a sea or an ocean. Such objects are during their use at least temporarily, or substantially always, at least partly in contact with the water. The object may be at least partly below the water (line) during use, or may substantially be all of its time below the water (line), such as for submarine applications.

Due to this contact with the water, biofouling may occur, with the above indicated disadvantages. Biofouling will occur at the surface of an external surface ("surface") of such object. The surface of an (element of the) object to be protected may comprise steel, but may optionally also comprise another material, such as e.g. selected from the group consisting of wood, polyester, composite, aluminium, rubber, hypalon, PVC, glass fiber, etc. Hence, instead of a steel hull, the hull may also be a PVC hull or a polyester hull, etc. Instead of steel, also another iron material, such as an (other) iron alloy may be used.

Herein, the term "fouling" or "biofouling" or "biological fouling" are interchangebly used. Above, some examples of fouling are provided. Biofouling may occur on any surface in water, or close to water and being temporarily exposed to water (or another aqueous liquid). On such a surface biofouling may occur when the element is in, or near water, such as (just) above the water line (like e.g. due to splashing water, such as for instance due to a bow wave). Between the tropics, biofouling may occur within hours. Even at moderate temperatures, the first (stages of) fouling will occur within hours; as a first (molecular) level of sugars and bacteria.

The anti-biofouling system comprises at least an UV emitting element. Further, the anti-biofouling system may comprise a control system (see also below), an electrical energy supply, such as a local energy harvesting system (see also below), etc. . . .

The term "anti-biofouling system" may also refer to a plurality of such systems, optionally functionally coupled to each other, such as e.g. controlled via a single control system. Further, the anti-biofouling system may comprise a plurality of such UV emitting elements. Herein, the term "UV emitting element" may (thus) refer to a plurality of UV emitting elements. For instance, in an embodiment a plurality of UV emitting elements may be associated to an external surface of the object, such as a hull, or may be comprised by such surface (see also below), whereas e.g. a control system may be configured somewhere within the object, such as in a control room or wheel house of a vessel.

The surface or area on which fouling may be generated is herein also indicated as fouling surface. It may e.g. be the hull of a ship and/or an emission surface of an optical medium (see also below). To this end, the UV emitting element provides UV radiation (anti-fouling light) that is applied to prevent formation of biofouling and/or to remove biofouling. This UV radiation (anti-fouling light) especially at least comprises UV radiation (also indicated as "UV light"). Hence, the UV emitting element is especially configured to provide UV radiation. Thereto, the UV emitting element comprises a light source. The term "light source" may also relate to a plurality of light sources, such as 2-20 (solid state) LED light sources, though many more light sources may also be applied. Hence, the term LED may also refer to a plurality of LEDs. Especially, the UV emitting element may comprise a plurality of light sources. Hence, as indicated above, the UV emitting element comprises one or more (solid state) state light sources. The LEDs may be (OLEDs or) solid state LEDs (or a combination of these LEDs). Especially, the light source comprises solid state LEDs. Hence, especially, the light source comprises a UV LED configured to provide one or more of UV-A and UV-C light (see also below). UV-A may be used to impair cell walls, whereas UV-C may be used to impair DNA. Hence, the light source is especially configured to provide the UV radiation. Herein, the term "light source" especially refers to a solid state light source.

Ultraviolet (UV) is that part of electromagnetic light bounded by the lower wavelength extreme of the visible spectrum and the X-ray radiation band. The spectral range of UV light is, by definition between about 100 and 400 nm (1 nm=$10^{-9}$ m) and is invisible to human eyes. Using the CIE classification the UV spectrum is subdivided into three bands: UV-A (long-wave) from 315 to 400 nm; UV-B (medium-wave) from 280 to 315 nm; and UV-C (short-wave) from 100 to 280 nm. In reality many photobiologists often speak of skin effects resulting from UV exposure as the weighted effect of UV wavelengths above and below 320 nm, hence offering an alternative definition. In literature, sometimes wavelengths around 400 nm are also indicated as "deep blue". Here, by definition UV radiation is radiation in the wavelength range of 100-400 nm. Beyond 400 nm, up to 780 nm, is herein indicated as visible radiation (visible light).

A strong germicidal effect is provided by the light in the short-wave UV-C band. In addition erythema (reddening of the skin) and conjunctivitis (inflammation of the mucous membranes of the eye) can also be caused by this form of light. Because of this, when germicidal UV-light lamps are used, it is important to design systems to exclude UV-C leakage and so avoid these effects. In case of immersed light sources, absorption of UV light by water may be strong enough that UV-C leaking is no problem for humans above the liquid surface. Hence, in an embodiment the UV radiation (anti-fouling light) comprises UV-C light. In yet another embodiment, the UV radation comprises radiation selected from a wavelength range of 100-300 nm, especially 200-300 nm, such as 230-300 nm. Hence, the UV radation may especially be selected from UV-C and other UV radiation up to a wavelength of about 300 nm. Good results are obtained with wavelengths within the range of 100-300 nm, such as 200-300 nm.

The element comprises an optical medium. The optical medium may have the function of a waveguide. Especially, the optical medium is provided as foil or plate (sheet). In specific embodiments, the light source is embedded in the optical medium. In this way, substantially all radiation escaping from the light source may be introduced in the optical medium and distributed over at least part of the optical medium. Therefore, the medium material is transmissive for light source radiation. The light source, such as a solid state light source, may be in physical contact with the optical medium. For instance, the LED die, or an optical element on the LED die, may be in physical contact with the medium material. Hence, the light source is especially embedded in the medium material.

However, in yet another embodiment one or more light sources may not be comprised in the optical medium. In such embodiments, radiation of the one or more light sources will pass through the optical medium, because of its transmissivity. In such embodiments, the one or more light sources are radiationally coupled to the optical medium. The term "radiationally coupled" especially means that the light source and the optical medium are associated with each other so that at least part of the radiation emitted by the light source is received by optical medium and transmitted thereby.

As indicated above, a suitable medium material comprises silicone. Even more especially, the medium material comprises a polydimethyl silicone. Especially, the silicone comprises a low amount of metal catalyst, such as a platinum catalyst, like less than 10 ppm, such as less than 5 ppm, even more especially less than 1 ppm. The invention is however not limited to silicone material as UV transmissive material (medium material). Also other (polymeric) materials may be applied that are transmissive for UV radiation, such as silica, fluoro polymers (such as teflon), and optionally (quartz) glass, etc. . . . Such materials are herein also indicated as "transmissive medium material".

The optical medium may also be provided as a (silicone) foil or plate for applying to the protected surface, the foil or plate comprising at least one light source for generating anti-fouling light and a sheet-like optical medium for distributing the UV radiation across the foil or plate.

In embodiments the foil or plate has a thickness in an order of magnitude of a couple of millimeters to a few centimeters, such as 0.1-10 cm, especially 0.1-5 cm, like 0.2-2 cm. In embodiments, the foil or plate is not substantially limited in any direction perpendicular to the thickness direction so as to provide substantially large foils or plates having sizes in the order of magnitude of tens or hundreds of square meters. The foil or plate may be substantially size-limited in two orthogonal directions perpendicular to the thickness direction of the foil or plate, so as to provide an anti-fouling tile; in another embodiment the foil or plate is substantially size-limited in only one direction perpendicular to a thickness direction of the foil or plate, so as to provide an elongated strip of anti-fouling foil or plate. Hence, the optical medium, and even also the lighting module, may be provided as tile or as strip. The tile or strip may comprise a (silicone) foil or plate. The tile may e.g. have dimensions like 0.01-10 m$^2$, such as 0.1-4 m$^2$, such as 0.1-1 m$^2$.

In an embodiment the lighting module comprises a two-dimensional grid of light sources for generating UV radiation and the optical medium is arranged to distribute at least part of the UV radiation from the two-dimensional grid of light sources across the optical medium so as to provide a two-dimensional distribution of UV radiation exiting the light emitting surface of the light module. The two-dimensional grid of light sources may be arranged in a chicken-wire structure, a close-packed structure, a rows/columns structure, or any other suitable regular or irregular structure. The physical distance between neigboring light sources in the grid may be fixed across the grid or may vary, for example as a function of light output power required to provide the anti-fouling effect or as function of the location of the lighting module on the protected surface (e.g. location on the hull of a ship). Advantages of providing a two-dimensional grid of light sources include that the UV radiation may be generated close to the areas to be protected with UV radiation illumination, and that it reduces losses in the optical medium or light guide and that it is increasing homogeneity of the light distribution. Preferably, the UV radiation is generally homogeneously distributed across the emission surface; this reduces or even prevents under-illuminated areas, where fouling may otherwise take place, while at the same time reducing or preventing energy waste by over-illumination of other areas with more light than needed for anti-fouling. In an embodiment, the grid is comprised in the optical medium. In yet another embodiment, the grid may be comprised by a (silicone) foil or plate.

Such grid may also be defined as a large area LED array, i.e. an arrangement of LEDs on a structure providing connection of the LEDs with suitable drive circuitry. Such structure typically has the form of a grid, comprising row electrodes and column electrodes, on which the LEDs are mounted in intersections between these electrodes.

Grids as defined above are amongst others described in WO2007122534, which is herein incorporated by reference. Hence, in an embodiment the two-dimensional grid of light sources comprises a large area LED array, comprising two stacks of electrodes and LEDs arranged in intersections of electrodes belonging to different stacks, wherein each electrode comprises a plurality of LED mounting surfaces, separated by electrode sections, each electrode section having two strip portions joined together by an connecting portion, said strip portions having a surface extension non-parallel to a planar extension of the LED array.

Further, in an embodiment the optical medium may be disposed proximate (including optionally attached to) the protected surface and coupled to receive the ultraviolet light, wherein the optical medium has a thickness direction perpendicular to the protected surface, wherein two orthogonal directions of the optical medium orthogonal to the thickness direction are parallel to the protected surface, wherein the optical medium is configured to provide a propagation path of the ultraviolet light such that the ultraviolet light travels within the optical medium in at least one of the two orthogonal directions orthogonal to the thickness direction, and such that, at points along a surface of the optical medium, respective portions of the ultraviolet light escape the optical medium.

Hence, in an embodiment the (anti-fouling lighting) system may comprise an optical medium, wherein the optical medium comprises a waveguide, such as an optical fiber, configured to provide said UV radiation (anti-fouling light) to the fouling surface. The surface of e.g. the waveguide from which the UV radiation (anti-fouling light) escapes is herein also indicated as emission surface. In general, this part of the waveguide may at least temporarily be submerged. Due to the UV radiation (anti-fouling light) escaping from the emission surface, an element of the object that is during use at least temporarily exposed to the liquid (such as seawater), may be irradiated, and thereby anti-fouled. However, the emission surface per se may also be anti-fouled. This effect is used in some of the embodiments of the UV emitting element comprising an optical medium described below.

Embodiments with optical media are also described in WO2014188347. The embodiments in WO2014188347 are herein also incorporated by reference as they are combinable with the control unit and/or water switch, and other embodiments, described herein.

As indicated above, the UV emitting element may especially comprise a UV radiation escape surface. Hence, in a specific embodiment the UV emitting element comprises a UV radiation escape surface, with the UV emitting element especially being configured to provide said UV radiation downstream from said UV radiation escape surface of said UV emitting element. Such UV radiation escape surface may be an optical window through which the radiation escapes from the UV emitting element. Alternatively or additionally, the UV radiation escape surface may be the surface of a waveguide. Hence, UV radiation may be coupled in the UV emitting element into the waveguide, and escape from the element via a (part of a) face of the waveguide. As also indicated above, in embodiments the radiation escape surface may optionally be configured as part of the external surface of the object.

The terms "upstream" and "downstream" relate to an arrangement of items or features relative to the propagation of the light from a light generating means (here the especially the first light source), wherein relative to a first position within a beam of light from the light generating means, a second position in the beam of light closer to the light generating means is "upstream", and a third position within the beam of light further away from the light generating means is "downstream".

However, as indicated above, in some embodiments the element may also be configured to provide visible light, instead of or in addition to UV radiation. In such embodiments, the term "UV emitting element" and similar terms may be replaced by "element" or "visible and/or UV emitting element", etc. . . .

The element further comprises an electrical connector for functionally coupling the light source with e.g. a source of electrical power external from the optical medium, wherein the electrical connector comprises a first connector part embedded in the optical medium and an interface connector part physically accessible from external from the optical medium. The electrical connector may be an electrical wire, in general with isolation surrounding the electrically conductive part. The electrical connector may power (when functionally connected with an electrical power source) the light source. Hence, the electrical connector may comprise a power cable, either with one electrical connector (single core) or with more electrical connectors (dual core, or more than two cores). Hence, the term "electrical connector" may also refer to a plurality of electrical connectors. In other embodiments the electrical connector may comprise an electrically conductive track. In yet a further embodiment, the electrical connector may comprise the power grid as defined above (for powering a plurality of associated light sources). The interface connector part is especially the part where locally the optical medium has an interface with the external and where the electrical connector may be approached from external. For instance, assuming a closed plate, with a face where the electrical connector penetrates the plate and has a part within the plate and a part external from the plate, it is precisely the position where the electrical connector penetrates the plate. It is also this position where water may migrate into the plate.

For providing electrical power from external, i.e. from outside the optical medium, to the light source(s) (and/) or other electrical components comprised by the optical medium, there is a part of the electrical connector that is accessible from external from the optical medium. This may e.g. include a feed through of a cable, or a socket, etc. . . . Especially at this interface, ingress of water may take place. The part that is accessible from external, especially for a functional coupling of an external power source, is indicated as interface connector part. The wires, cables, electrically conductive tracks comprised by the optical medium are especially indicated as first connector part. Hence, the term "first connector part" may also refer to a plurality of first connector parts. Hence, seen from external starting from the interface connector part the electrical connector is embedded in the optical medium. Note that when a cable is used which includes a part of its lengths outside the optical medium and embedded over part of its length in the optical medium, the cross section at the interface of the optical medium where the cable gets into (or comes out from) the optical medium may be considered the interface connector part. Hence, the term "interface connector part" does not necessarily indicate a separate device but may especially indicate a position.

Hence, the phrase "for functionally coupling the electrical component external to the optical medium" especially indicates that the electrical connector is configured to provide a functional coupling between the electrical component and another component, especially an electrical component, even more especially an electrical power source and/or a control system external from the optical medium.

To prevent or reduce (the effect of) such ingress of water the element further comprises a water barrier. The water barrier ("barrier" or "water stop") is at least partly embedded in the optical medium and configured to enclose at least part of the first connector part of the electrical connector and may especially be configured adjacent to the interface connector part. Especially, the water barrier is (also) entirely embedded in the medium material.

Especially, the water barrier is configured to adhere to the medium material and the electrical connector. It appears that the medium material does not adhere very well to the first connector part. This may be due to the fact that for a good transmissivity, the medium material, especially siloxane, should include no or a low amount of adhesives or adhesion promoters. This relative bad adhesion facilitates water ingress. Hence, with such water barrier, having a good adhesion to both the first electrical connection part and the optical material, a barrier function may be provided. Such water barrier may, if necessary, include a high amount of adhesive or adhesion promoters. As this water barrier is only locally applied, the influence on the optical properties of the optical medium may be relatively low. In a specific embodiment, the water barrier comprises a silicone adhesive, also known as silicone sealant. Examples of suitable silicone adhesives are e.g. Dow Corning 748, Momentive 5240, Loctite clear silicone. Examples of adhesion promoters are e.g. Dow Corning 1200 OS, ACC primer no. 3, etc.

In a specific embodiment the water barrier comprises an envelope, especially a glass envelope, especially a tubular (glass) envelope, configured to enclose at least part of the first connector part and having a length (l) selected from the range of at least 0.1 mm, such as 0.1-50 mm, like in the range of 0.2-50, such as 1-30 mm, like 5-25 mm. The (glass) envelope may be configured to circumferentially enclose part of the first electrical connector, such as over the indicated length. However, other envelopes may be used as well, and other shapes than tubular may also be used as well. For instance, also e.g. spherical shaped envelopes may be applied, or optionally cubic or rectangular shaped.

There may be a small mismatch in cross-sectional area, in the sense that the envelope may have a slightly larger cross-sectional area, such as 5-20% larger. This may provide a gap between the first connector part and the envelope. This gap may be used to fill with silicone adhesive for a good closure and adhesion. Hence, in a specific embodiment at least part of the silicone adhesive is configured between the electrical connector and the tubular glass envelope.

Alternatively, the cross-sectional area may substantially be identical. In yet further embodiment, the envelope is over substantially its entire length in physical contact with the first connector part. For instance, a polymeric material forming the envelope may be cured and/or applied with heat to the first connector part. This may provide a tight closure.

Especially, the envelope comprises an envelope material that is light transmissive. The material may comprises one or more materials selected from the group consisting of a transmissive organic material, such as selected from the group consisting of PE (polyethylene), PP (polypropylene), PEN (polyethylene napthalate), PC (polycarbonate), polymethylacrylate (PMA), polymethylmethacrylate (PMMA) (Plexiglas or Perspex), cellulose acetate butyrate (CAB), silicone, polyvinylchloride (PVC), polyethylene terephthalate (PET), including in an embodiment (PETG) (glycol modified polyethylene terephthalate), PDMS (polydimethylsiloxane), and COC (cyclo olefin copolymer). Especially, the material may comprise an aromatic polyester, or a copolymer thereof, such as e.g. polycarbonate (PC), poly (methyl)methacrylate (P(M)MA), polyglycolide or polyglycolic acid (PGA), polylactic acid (PLA), polycaprolactone (PCL), polyethylene adipate (PEA), polyhydroxy alkanoate (PHA), polyhydroxy butyrate (PHB), poly(3-hydroxybutyrate-co-3-hydroxyvalerate) (PHBV), polyethylene terephthalate (PET), polybutylene terephthalate (PBT), polytrimethylene terephthalate (PTT), polyethylene naphthalate (PEN); especially, the material may comprise polyethylene terephthalate (PET). Hence, the material is especially a polymeric material. However, in another embodiment material may comprise an inorganic material. Preferred inorganic materials are selected from the group consisting of glasses, (fused) quartz, transmissive ceramic materials, etc. . . . Also hybrid materials, comprising both inorganic and organic parts may be applied, such as silicones. Especially preferred are PMMA or glass as material for the envelope.

In general, the electrical connector comprises one or more electrically conductive tracks with an isolator surrounding the one or more electrically conductive tracks. However, other options are also possible.

In a specific embodiment, the water barrier may comprise a glass barrier that is in physical contact with the electrically conductive track. Hence, in such embodiment a glass-metal connection may be used as water barrier—electrical conductive track. For instance, one may provide an electrical conductor without isolator or one may provide an electrical conductor with isolator and remove a part of the isolator, such as a 0.1-50 mm, such as 1-30 mm, like 5-25 mm. At the position where the isolator is removed, the glass can be melted around the electrical conductor. Hence, in a specific embodiment at a position of the water barrier the electrical connector consists of metal and wherein the water barrier comprises a glass forming a metal glass connection. The metal glass connection is especially configured to provide a water tight connection. Such metal glass connection can thus also be used to prevent (further) ingress of water.

Therefore, the material of the water barrier is especially selected such, that in combination with the electrical connector, especially the first connector part, and the medium material, a water tight barrier is created. The water barrier may form an interface with the medium material and an interface with the electrical connector, especially in embodiments its isolator, which substantially blocks transport of water along the electrical connector.

In general, the water barrier will be arranged relatively close to the interface connector part. In an embodiment, the water barrier may also penetrate through the medium material to the external. However, in other embodiments the water barrier is entirely comprised by the optical medium (material). In a specific embodiment, the water barrier is configured at a first distance (d1) selected from the range of 1-400 mm from the interface connector part.

The water barrier thus especially comprises a material composition different from the optical medium. For instance, the optical medium may comprise silicone, whereas the water barrier may comprise a silicone adhesive. In yet another example, the optical medium may comprise a silicone, whereas the water barrier comprises glass. In yet a further example, the optical medium comprises a silicone, whereas the water barrier comprises glass and an adhesive configured between the glass and the electrical connector.

Especially in the case of a plurality of light sources, a grid can be provided which, even when a single connection is broken, still substantially all light sources may still be powered. Therefore, a damage or even break of the optical medium may not be a problem in view of lighting aspects. However, in view of water ingress this may be rather problematic. Hence, the invention also provides an optical medium with a plurality of second water barriers (in addition to the water barrier close to the interface connector part). Therefore, in yet a further embodiment the element may comprise: (i) a plurality of light sources, (ii) said optical medium, wherein the plurality of light sources are embedded in the optical medium, an electrical connector infrastructure for functionally coupling the plurality of light sources with a source of electrical power external from the optical medium, wherein the electrical connector infrastructure comprises one or more interface connector parts and a plurality of first connector parts functionally coupled to the plurality of light sources, and (iv) a plurality of water barriers distributed over the element, with especially at least one water barrier configured adjacent to the interface connector part of one of the one or more interface connector parts. For instance, the element may comprise 1-2000 water barriers per $m^2$ optical medium, such as 10-1600 water barriers per $m^2$ optical medium.

In an embodiment, wherein a plurality of light sources is applied, which are electrically connected via electrical connector parts, thereby providing a plurality of interconnecting electrical connector parts, at least 20%, such as at least 40%, like even at least 60%, or even 80% or more, such as up to 100% of the interconnecting electrical connector parts may include one or more water barriers. Hence, in a specific embodiment the invention also provides an element wherein a subset of one or more light sources are functionally coupled with one or more first connector parts, wherein all first connector parts comprise one or more water barriers. The subset may include one or more electrical components, such as light sources. Optionally all electrical components are surrounded by water barriers, in the sense that each electrical connector in functional contact with the electrical components comprises a water barrier. Hence, seen from the electrical component, each electrical connector is enclosed by a water barrier before another electrical component (inside or outside optical medium).

In yet a further aspect the invention also provides a method for providing an object with the element as defined herein, the method comprising (i) associating the element to an external surface of said object and functionally coupling to an electrical power source. In embodiments, this may imply that the element, more especially the optical medium is configured as a kind of second skin to the external surface. Hence, the element provides radiation downstream from an optical medium surface, escaping in a direction away from the external surface.

In yet a further aspect, the invention provides a method for providing the element as defined herein, wherein the method comprises (i) providing a functional combination of (a) an electrical component, (b) an electrical connector for functionally coupling the electrical component with a source of electrical power, and (c) a water barrier configured to enclose at least part of the electrical connector; and (ii) encapsulating the light source, part of the electrical connector and at least part of the water barrier with medium material comprising a silicone transmissive for the light source radiation, to provide said element. Especially, the electrical component may be a light source. Yet more especially the electrical component refers to a plurality of light sources, such as e.g. the grid as defined above. Even more especially, the invention provides a method for providing the element as defined herein, the method comprising: (i) providing a functional combination of (a) a light source configured to provide light source radiation in one or more of the UV and the visible, (b) an electrical connector for functionally coupling the light source with a source of electrical power external, wherein the electrical connector comprises a first connector part (and an interface connector part), and (c) a water barrier configured to enclose at least part of the first connector part of the electrical connector (and configured adjacent to the interface connector part); and (ii) encapsulating the light source, the first connector part and the water barrier with medium material, comprising a silicone transmissive for the light source radiation, to provide said element.

As indicated herein, the element may be configured for preventing biofouling on a surface that is in contact with water. Hence, the element may be indicated as element for preventing biofouling on a surface that is in contact with water. Instead of the term element, (in embodiments) also the term "device" or "apparatus" may be applied. As indicated herein, the water barrier is especially configured to enclose at least part of the electrical connector. Hence, the water barrier encloses at least part of the electrical connector. Especially, the water barrier encloses the electrical connector over part of the length of the electrical connector. The water barrier can e.g. be configured as a (kind of) sleeve.

BRIEF DESCRIPTION OF THE DRAWINGS

Embodiments of the invention will now be described, by way of example only, with reference to the accompanying schematic drawings in which corresponding reference symbols indicate corresponding parts, and in which.

The schematic drawings are not necessarily on scale.

DETAILED DESCRIPTION OF THE EMBODIMENTS

Figure 1A:
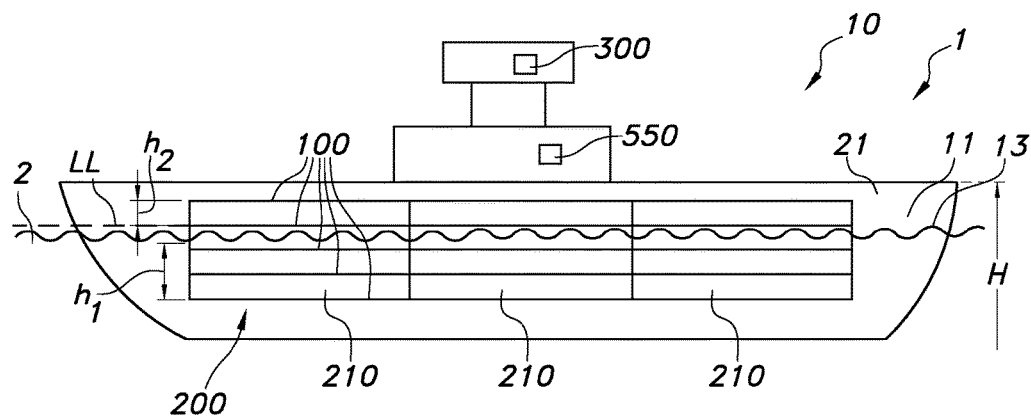
FIGS. 1a-1g schematically depict some aspects of the element of objects comprising such element.

FIG. 1a schematically depicts a vessel 1 comprising a hull 21. Reference 13 indicates the water line of water 2. Reference 300 indicates an optional control system, especially configured to control the anti-biofouling system, which is further elucidated below. FIG. 1a schematically depicts an embodiment wherein a vessel 1, as embodiment of the object 10, comprises a plurality of anti-biofouling systems 200 and/or a one or more of such anti-bio fouling systems 200 comprising a plurality of radiation emitting elements 210, further described as UV emitting elements. For instance, dependent upon the height of the specific such anti-biofouling system 200 and/or the height of the UV emitting elements 210, such as relative to a water (line), the respective UV emitting elements 210 may be switched on. FIG. 1a also indicates the load line LL. For instance, about 0.5-2 m above, indicated with h2, and about 0.5-2 m below, indicated with h1, the load line LL, the UV emitting elements 210 may be applied. Further, the control system 300 may be configured to control the anti-biofouling system 200. Reference 550 indicates an electrical power source for powering the system 200 or the light sources (see further also below) of the element 210. The elements 210 may e.g. have areas in the range of 0.01-10 m².

Figure 1B:
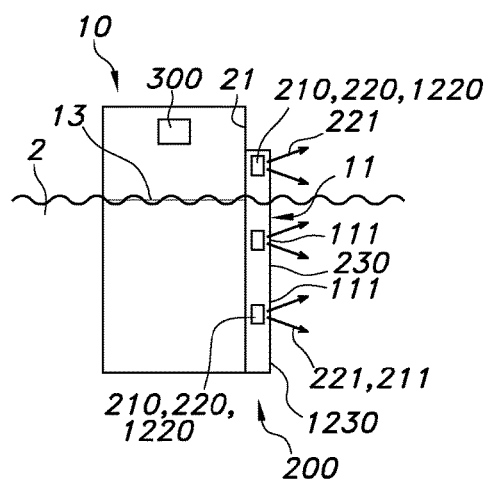
Figure 1C:
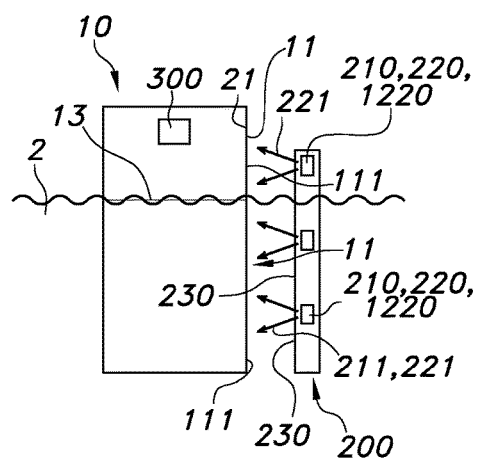

FIGS. 1b-1c schematically depict embodiments of an object 10 that during use is at least partly submerged in water 2, see the water line 13. The object 10, such as a vessel or a sluice, see also below, further comprises an anti-biofouling system 200 comprising an UV emitting element 210, especially for application of UV radiation 221 to a part 111 of an external surface 11 of the object 10, such as a hull or part or a hull. Here, two embodiments are shown wherein the anti-biofouling system 200, or more especially the UV emitting element 210, is part of an outer surface, and thereby forms in fact part of the outer surface (FIG. 1b) or wherein the UV emitting element 210 is configured to irradiate the outer surface and does not necessarily form part of an outer surface, such as a hull of a ship (FIG. 1c). For instance, the object 10 is selected from the group consisting of a vessel 1 and an infrastructural object 15 (see also below). Especially, the element 210 is configured against the external surface 11, thereby providing a new external surface. This external surface is indicated with reference 1230. Reference 230 indicates the radiation escape surface. Light source radiation 221 escapes from this surface to the external. Herein, the invention is especially elucidated with reference to UV radiation, but additionally or alternatively, the radiation 221 may also include visible light or a combination of visible and UV radiation. For anti-fouling purposes, the radiation 221 especially at least includes UV radiation. In FIG. 1b, the element 210, especially the optical medium 270, is provided as conformal coating to the external surface 11. The light source 220 is configured to provide light source radiation 221. This may escape from the optical medium 270 as element radiation 211. The element radiation 211 may optionally include converted light source radiation 221 or may substantially consist of the light source radiation 221, such as UV radiation. Reference 1220 indicates an electrical component. Here, light sources 220 are uses as electrical component 1220, or are comprised by the electrical component 1220. Note that also other types of electrical components may be used alternatively or in addition (see also above).

The UV emitting element 210 comprises one or more light sources 220 and may thus especially be configured to irradiate with said UV radiation 221 (during an irradiation stage) one or more of (i) said part 111 of said external surface 11 and (ii) water adjacent to said part 111 of said external surface 11. The former variant applies especially the embodiment of FIG. 1c, and the latter embodiment especially applies to both embodiments of FIGS. 1b-1c. Note however that when an external surface of the UV emitting element 210 is configured as external surface of the object 10, of course the part 111 is irradiated per se with the UV radiation 21.

Hence, the UV emitting element 210 comprises a UV radiation escape surface 230 and the UV emitting element 210 is configured to provide said UV radiation 221 downstream from said UV radiation escape surface 230 of said UV emitting element 210.

Especially, the light source 220 is at least controllable between a first UV radiation level and a second UV radiation level, wherein the first UV radiation level is larger than the second UV radiation level (and wherein the second UV radiation level is smaller than the first radiation level (including e.g. zero)).

In a specific embodiment, the object 10 further comprises a control system 300 configured to control said UV radiation 221.

Figure 1D:
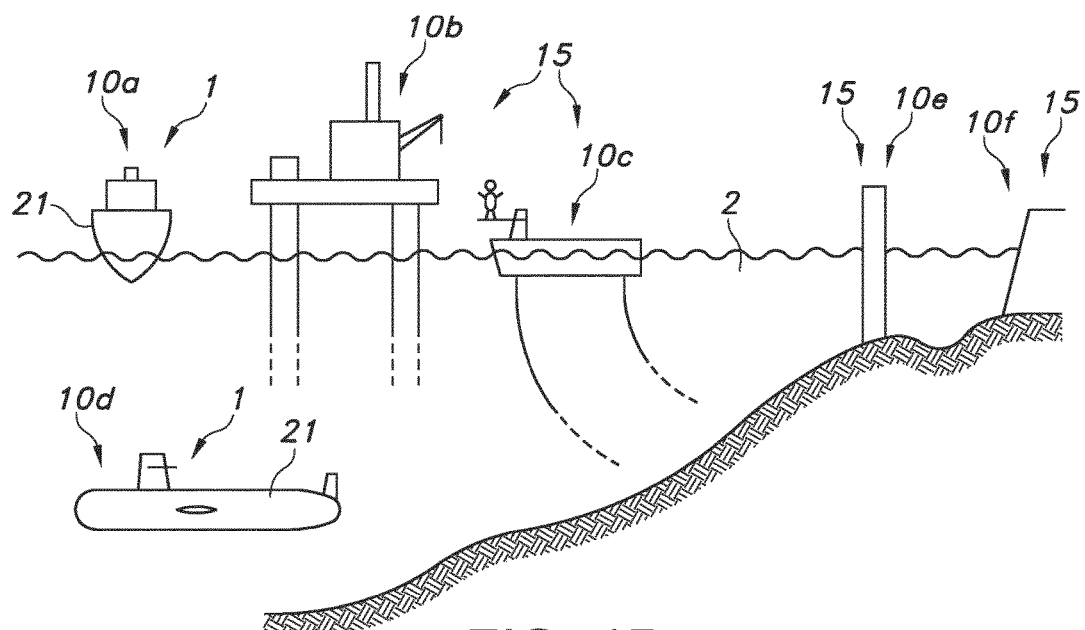

As indicated above, the term "vessel", indicated with reference 1, may e.g. refer to e.g. a boat or a ship (ref 10a in FIG. 1d), etc., such as a sail boat, a tanker, a cruise ship, a yacht, a ferry, a submarine (ref. 10d in FIG. 1d), etc. etc. . . . , like schematically indicated in FIG. 1d. The term "infrastructural object", indicated with reference 15, may especially refer to aquatic applications that are in general arranged substantially stationary, such as a dam/sluice (references 10e/10f in FIG. 1d), a pontoon (ref. 10c in FIG. 1d), an oilrig (ref. 10b in FIG. 1d), etc. etc. . . . Note that the invention may also be applied to other devices or apparatus (see also above).

Figure 1E:
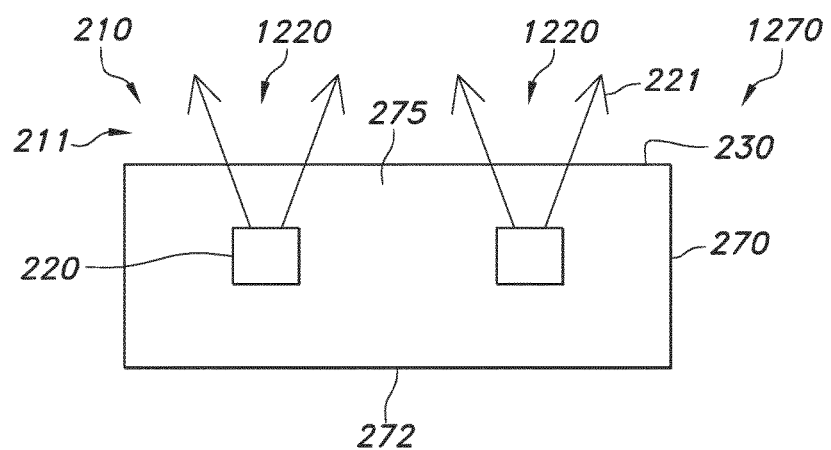

FIG. 1e schematically the UV emitting element 210 or the optical medium 270 /optical medium unit 1270. The light sources 220 are at least partly integrated in the optical medium 270. In this way, UV radiation (and/or other radiation in the visible) can easily be distributed through the waveguide or optical medium 270. Reference 272 indicates the second optical medium surface, opposite of the radiation escape surface 230. The second optical medium surface 272 may optionally include a reflector. However, other options may also be possible, see FIG. 1g.

Figure 1F:
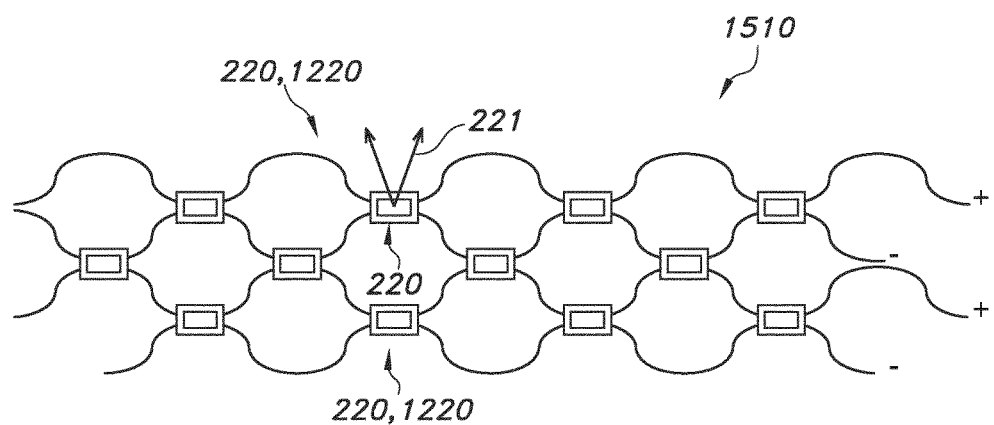

FIG. 1f shows a chicken-wire embodiment where light sources 220, such as UV LEDs, are arranged in a grid and connected in a series of parallel connections. The LEDs can be mounted at the nodes either through soldering, glueing or any other known electrical connection technique for connecting the LEDs to the chicken wires. One or more LEDs can be placed at each node. DC or AC driving can be implemented. If AC is used, then a couple of LEDs in anti parallel configuration may be used. The person skilled in the art knows that at each node more than one couple of LEDs in anti parallel configuration can be used. The actual size of the chicken-wire grid and the distance between UV LEDs in the grid can be adjusted by stretching the harmonica structure. The chicken-wire grid may be embedded in an optical medium. Note that damages of a wire may not necessarily lead to a dead LED spot. The grid or electrical infrastructure is indicated with reference 1510.

Figure 1G:
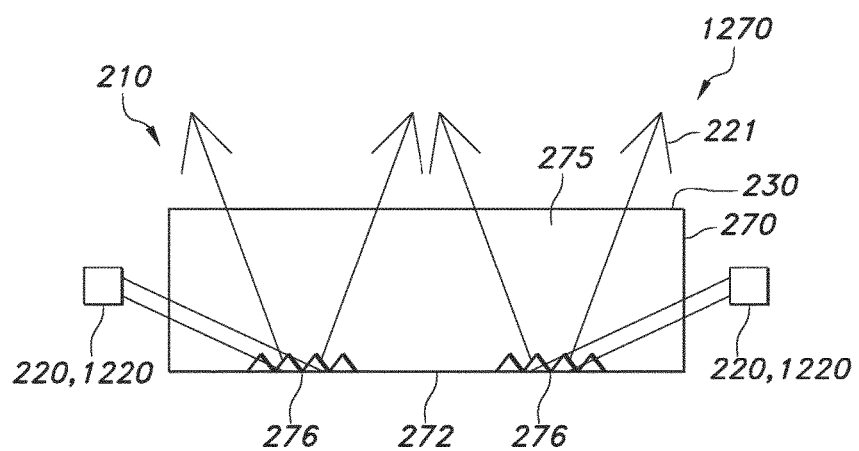

FIG. 1g schematically shows a variant based on FIG. 1e. In this variant, the light sources 220 are configured external from the optical medium 270. Especially, in such instance (though the former variant may optionally also include outcoupling structures), the optical medium 270 may comprise outcoupling structures 276 which are configured to couple the UV radiation 221 out via the radiation escape surface 230. Hence, the outcoupling structures may especially be configured at and/or close to the second optical medium surface 272.

Amongst others, the invention provides a water lock (water barrier) added to a cable at a position close to the edge of the silicone sheet, just before the cable exits the silicone. This water lock can be made of a glass ring around the cable. In general silicones adhere very well to glass, also without adhesion promoters. The glass ring can be fused with the plastic mantle of the cable, or glued with highly adhering glue. Hence, the water barrier may circumferentially enclose the electrical connector over a part of the length of the electrical connector.

In an embodiment, a water lock can be applied on several locations divided over the wire grid in the silicone sheet, thereby creating cells. When part of a large sheet is damaged, only that cell is lost. Water cannot enter the surrounding cells by creeping along the wires, because it will encounter the water stop of the next cell.

The water lock can be added by pre-dipping the LEDs, wires and cable in a well-adhering silicone, thus creating a thin coating layer. This thin layer has then a good adhesion to the embedding optical grade silicone. The well adhering thin silicone layer has less optical transmission and will decrease efficiency of the whole system, but this will be very low due to its thin dimension.

In an embodiment, a water lock can be added that at the same time serves as connector. The connector is placed at the edge of the silicone and is made of high moisture barrier material with a very good adhesion to the embedded electrical wires. The outside cable is plugged into this connector and sealed with a non-optical well adhering (silicone) sealant. The connector can also be made of an electrically conductive material, so the wires are not connected directly to the outgoing cable.

Figure 2A:
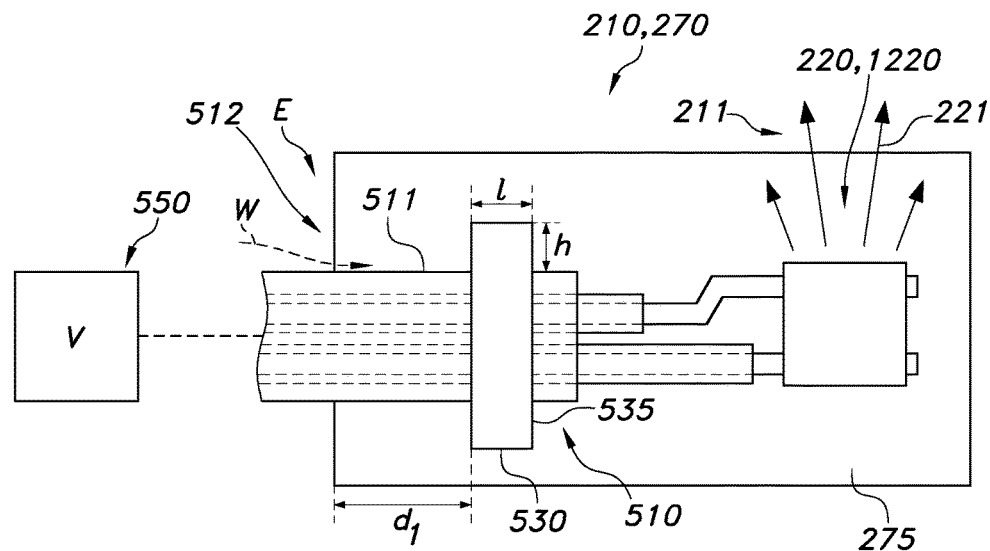
FIGS. 2a-2g schematically depict some further aspects and variants of the element.

Hence, FIG. 2a schematically depicts an embodiment of the element 210 configured to provide element radiation 211 comprising one or more of UV radiation and visible radiation. The element 210 comprises a light source 220 configured to provide light source radiation 221 in one or more of the UV and the visible. The element 210 further comprises an optical medium 270 comprising medium material 275, such as a silicone, which is transmissive for the light source radiation 221. The light source 220 is embedded in the optical medium 270. The optical medium further comprises an electrical connector 510 for functionally coupling the light source 220 with a source of electrical power external from the optical medium 270. As shown, the electrical connector 510 comprises a first connector part 511 embedded in the optical medium 270 and an interface connector part 512 physically accessible from external from the optical medium 270. Basically, the interface connector part can be seen as the part of the electrical connector that is configured between the interface of external and optical medium material 275. In this embodiment, this is the part that extends into the external E. A water barrier 530 is provided, which is at least partly embedded in the optical medium 270. The water barrier is configured to enclose at least part of the first connector part 511 of the electrical connector 510 and configured adjacent to the interface connector part 512. The water barrier 530 prevents water ingress or at least further transport of water along the electrical connector 510. The water barrier 530 has a length or width 1, i.e. the length parallel to the electrical connector 510. The height is indicated with reference h, and may e.g. (also) be in the range of 0.1-50 mm. Reference 535 indicates the water barrier material, which may thus especially be silicone. The term "water barrier material" may also refer to a plurality of materials. FIG. 2a also shows with dashed line W a possible ingress of water. As the water barrier 530 is configured to adhere well with the medium material 275 and with the electrical connector 510, water is blocked for further ingress. Water might intrude along the cable, as the adhesion between the cable and the optical medium material 275 may be suboptimal. However, when the water meets the water barrier 530, this water barrier 530 may adhere well to the electrical connector 510 or cable and to the optical medium material 275, thereby effectively blocking further ingress.

Figure 2B:
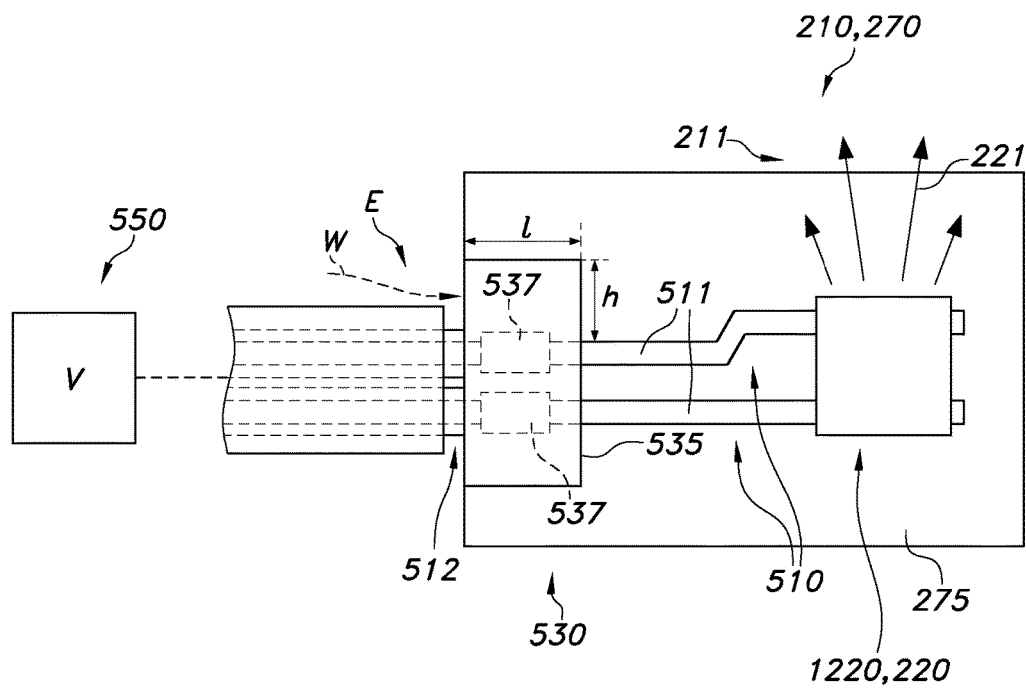

FIG. 2b schematically depicts a similar embodiment. In this embodiment however, part of the electrical conductive track, which is in general copper, is replaced by an electrically conductive silicone 537. Now, the water barrier 530 may substantially consist of only silicones, including the electrical connector part 512 also comprising silicone.

Figure 2C:
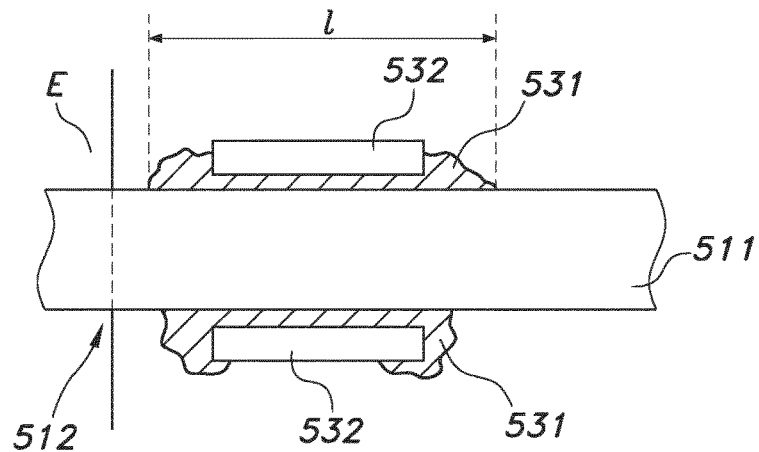
Figure 2D:
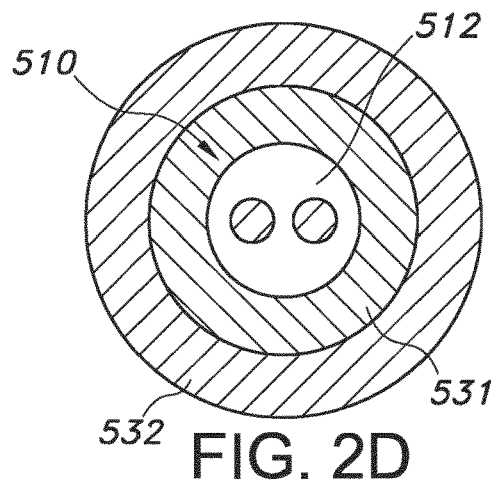

FIG. 2c schematically depicts an embodiment wherein the water barrier 530 comprises a tubular glass envelope 532 configured to enclose at least part of the first connector part 511 and having a length 1 selected from the range of 0.1-50 mm. Further, the water barrier 530 comprises a silicone adhesive 531. In this schematically depicted embodiment at least part of the silicone adhesive 531 is configured between the electrical connector 510 and the tubular glass envelope 532. A cross sectional view is shown in FIG. 2d, wherein by way of example the electrical connector comprises two conductive tracks (dual core). As indicated above, basically the interface connector part 512 can be seen as the part of the electrical connector that is configured between the interface of external and optical medium material 275. This interface part 512 is indicated with the dashed line. At one side, the electrical connector extends to the exterior E and at the other side the electrical connector part is embedded as first (electrical) connector part 511. Hence, the interface part can be a plane, or a virtual plane/circumference. As can be seen from FIGS. 2c and 2d, the water barrier in these, but also other embodiments, may circumferentially enclose the electrical connector over a part of the length of the electrical connector. The water barrier is thus especially in physical contact with the electrical connector over the part of the length of the electrical connector. In this way, a water barrier is provided which may essentially block water from migrating along the electrical connector.

Figure 2E:
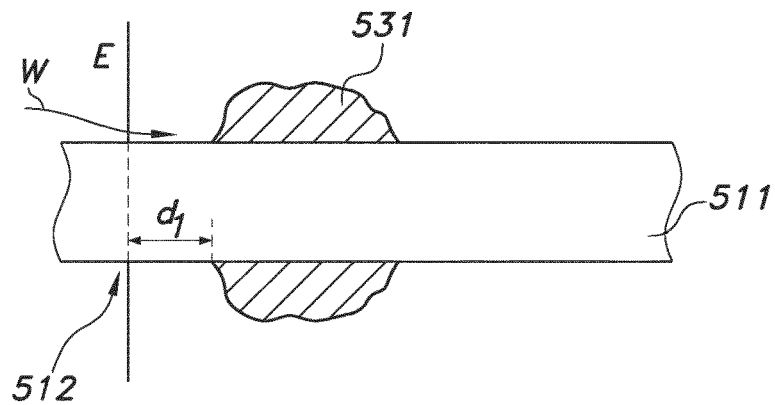

In FIG. 2e, schematically an embodiment is depicted wherein the water barrier 530 essentially comprises a silicone adhesive 531.

Figure 2F:
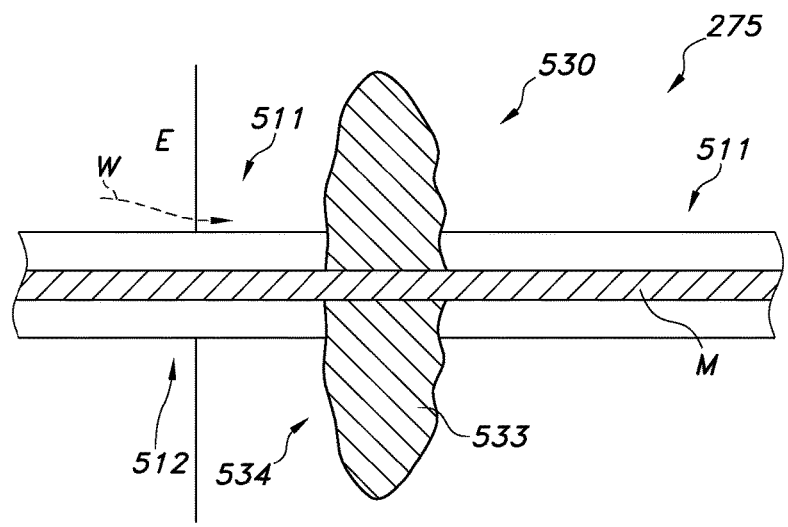

FIG. 2f schematically depicts an embodiment wherein at a position of the water barrier 530 the electrical connector consists of metal (conductor) M, such as copper, and wherein the water barrier 530 comprises a glass 533 forming a metal glass connection 534.

Figure 2G:
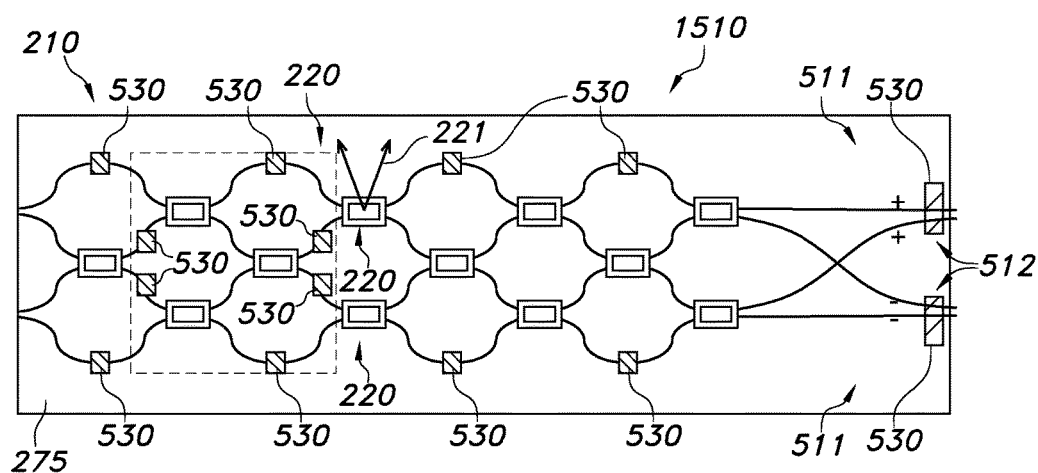

FIG. 2g schematically depicts an embodiment of the element 210 comprising a plurality of light sources 220 embedded in the optical medium 270. Further, the element 210 comprises an electrical connector infrastructure 1510 for functionally coupling the plurality of light sources 220 with a source of electrical power external from the optical medium 270. The electrical connector infrastructure 1510 comprises one or more interface connector parts 512 and a plurality of first connector parts 511 functionally coupled to the plurality of light sources 220. Further, the element comprises a plurality of water barriers 530 distributed over the element 210, with at least one water barrier 530 configured adjacent to the interface connector part 512 of one of the one or more interface connector parts 512. Note that two water barriers 530 are arranged close to the interface connector parts 512. Further, a plurality of other barriers are distributed over the element 210, especially the optical medium 270 (embedded therein). The water barriers 530 may further be configured to surround one or more light sources 220. Hence, all parts of first connector parts 511 functionally coupled with a subset of one or more light sources 220 may be provided with water barriers 530. In that way, a kind of compartment or section is made within which one or more light sources 220 are safeguarded from water ingress. For instance, even when the optical medium 270 would include a breakage one or more compartments might be protected from water ingress. Hence, for instance sections of LEDs may be safeguarded: when one or more wires are damaged or exposed to water, LEDs within such compartment or section would not substantially be at risk, see also the section indicated with the dashed line. All light sources 220, such as LEDs, are protected by water barriers 530.

The term "substantially" herein, such as in "substantially all light" or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

The invention claimed is:

1. An element comprising:
an electrical component;
an optical medium,
   wherein the optical medium comprises medium material, wherein the medium material comprises a silicone,
   wherein the silicone is transmissive for at less one of UV radiation and visible radiation,
   wherein the electrical component is embedded in the optical medium;
an electrical connector,
   wherein the electrical connector is external to the optical medium,
   wherein the electrical connector is arranged to functionally couple to the electrical component,
   wherein the electrical connector is embedded in the optical medium over at least part of its length; and
a water barrier, the water barrier comprising a silicon adhesive,
   wherein the silicon adhesive is at least partly embedded in the optical medium,
   wherein the silicone adhesive is configured to enclose at least part of the electrical connector.

2. The element according to claim 1, wherein the water barrier is configured to adhere to the medium material and the electrical connector, and wherein the water barrier comprises a silicone adhesive.

3. The element according to claim 1, wherein the water barrier comprises
a tubular glass envelope, the tubular glass envelope having a length selected in a range of 0.1-50 mm, wherein the tubular glass envelope is configured to enclose at least part of the first connector part.

4. The element according to claim 1, wherein at a position of the water barrier, the electrical connector consisting of metal and wherein the water barrier forming a water tight connection.

5. The element according to claim 1, wherein the medium material comprises a polydimethyl silicone.

6. The element according to claim 1, wherein the electrical connector comprises:
- a first connector part, the first connector part embedded in the optical medium, and
- an interface connector part, wherein the first connector part is physically accessible external to the optical medium, and wherein the water barrier is configured at a first distance selected from a range of 1-400 mm from the interface connector part.

7. The element according to claim 1, comprising 1-2000 water barriers per m$^2$ optical medium.

8. The element according to claim 1,
wherein the electrical component comprises a light source, wherein the light source is configured to provide light source radiation in one or more of the UV and the visible wavelength ranges;
wherein the light source is embedded in the optical medium;
wherein the electrical connector is arranged to functionally coupling the light source with a source of electrical power external to the optical medium, wherein the electrical connector comprises:
- a first connector part embedded in the optical medium; and
- an interface connector part where the first connector part is physically accessible external to the optical medium.

9. The element according to claim 8, further comprising:
a plurality of light sources embedded in the optical medium;
an electrical connector infrastructure, wherein the electrical connector infrastructure is arranged to functionally couple the plurality of light sources with the source of electrical power, wherein the electrical connector infrastructure comprises a plurality of first connector parts functionally coupled to the plurality of light sources; and
a plurality of the water barriers distributed over the electrical connector infrastructure.

10. The element according to claim 8, wherein a subset of the plurality of light sources are functionally coupled with one or more first connector parts, wherein all first connector parts comprise at least one of the plurality of the water barriers.

11. The element according to claim 8, wherein the element is configured to provide element radiation comprising UV radiation.

12. A system comprising:
the element according to claim 1, and
a control system, the control system configured to control radiation from the element.

13. An object comprising:
the element according to claim 1, wherein the element is associated with an external surface of the object, wherein the object further comprises an electrical power source, wherein the electrical power source is configured to provide electrical power to the element.

14. A method for providing an object with the element according to claim 1, the method comprising:
associating the element with an external surface of the object, and
functionally coupling the element to an electrical power source.

15. An element comprising:
a functional combination of:
an electrical component,
an electrical connector, wherein the electrical connector is configured to:
couple the electrical component with a source of electrical power, and
a water barrier, the water barrier configured to enclose at least part of the electrical connector; and
an optical medium configured to
encapsulate a light source, part of the electrical connector and the water barrier, wherein the optical medium comprises a silicone material optically transmissive to radiation of the light source.

* * * * *